United States Patent [19]

Tsujimoto et al.

[11] Patent Number: 4,735,744
[45] Date of Patent: Apr. 5, 1988

[54] NOVEL BENZOQUINONE DERIVATIVES AND PRODUCTION PROCESS THEREOF AS WELL AS USE AS COLOR-DEVELOPERS SUITABLE FOR RECORDING MATERIALS

[75] Inventors: Michihiro Tsujimoto, Tokyo; Kiyoharu Hasegawa, Yokohama; Hiroyuki Akahori, Yokosuka; Eishi Tanaka, Kamakura; Makoto Asano, Yokohama, all of Japan

[73] Assignee: Mitsui Toatsu Chemicals, Incorporated, Tokyo, Japan

[21] Appl. No.: 738,348

[22] Filed: May 28, 1985

[30] Foreign Application Priority Data

Jun. 7, 1984 [JP] Japan ............... 59-115437
Oct. 16, 1984 [JP] Japan ............... 59-215219
Mar. 18, 1985 [JP] Japan ............... 60-53846

[51] Int. Cl.$^4$ ............... C07C 50/04
[52] U.S. Cl. ............... 260/396 R
[58] Field of Search ............... 260/396 R

[56] References Cited

U.S. PATENT DOCUMENTS 3,282,968 11/1966 Scriber ............... 260/396
3,387,004 6/1968 Mosby et al. ............... 260/396
4,398,753 8/1983 Asano et al. ............... 282/27.5

FOREIGN PATENT DOCUMENTS 57-107882 7/1982 Japan.
185237 11/1982 Japan ............... 260/396 R
59-188528 10/1984 Japan.

OTHER PUBLICATIONS

Gowan et al, *Noise Index of Organic Reactions*, 1962, p. 123, #342.

*Primary Examiner*—Glennon H. Hollrah
*Assistant Examiner*—Raymond Covington
*Attorney, Agent, or Firm*—Fisher, Christen & Sabol

[57] ABSTRACT

Disclosed herein is a novel benzoquinone derivative represented by the following general formula (I):

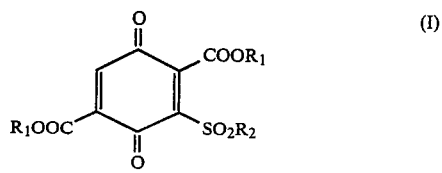

wherein $R_1$ means an alkyl or cycloalkyl group, $R_2$ denotes an alkyl or cycloalkyl group, a phenyl group which may optionally contain one or more halogen atoms and/or alkyl, cycloalkyl, alkoxy, alkylene, phenoxy, phenyl and/or biphenylyl groups, or a benzyl or naphthyl group which may optionally contain one or more methyl groups. This compound is useful as an oxidative color-developing agent for recording materials.

5 Claims, No Drawings

NOVEL BENZOQUINONE DERIVATIVES AND PRODUCTION PROCESS THEREOF AS WELL AS USE AS COLOR-DEVELOPERS SUITABLE FOR RECORDING MATERIALS

TECHNICAL FIELD

This invention relates to novel benzoquinone derivatives and their production process as well as the use as color-developing agents suitable for recording materials. More specifically, it relates to novel benzoquinone derivatives and their production process as well as utility of the benzoquinone derivatives as color-developing agents for causing colorless dyestuff precursors (chromogenic reactants) to produce their colors upon contact between the benzoquinone derivatives and dyestuff precursors.

BACKGROUND ART

Pressure-sensitive recording paper sheets, heat-sensitive recording paper sheets and the like are adapted to effect copying and/or recording by making use of color-producing reactions which respectively take place by causing electron-donating dyestuff precursors and electron-attracting acidic color-developing agents to contact with each other by pressures or heat. Reflecting recent rationalization of office work and increased utilization of facsimile facilities, these pressure-sensitive recording paper sheets, heat-sensitive recording paper sheets and the like have found wide-spread commercial utility.

In each of pressure-sensitive copying paper sheets which are widely used these days, the coated side of a sheet (a), which has been prepared by dissolving a dyestuff precursor such as triphenylmethanephthalide- or fluoran-type dyestuff precursor in a hydrophobic solvent, microencapsulating the thus-obtained solution in a manner known per se in the art and then coating the resultant microcapsules on a base material such as paper sheet or the like, is brought into a contiguous relation with the coated side of another sheet (b) bearing an oil-absorbing or oilsoluble acidic color-developing agent such as acid clay, a phenol-formaldehyde polymer or a metal salt of a salicylic acid derivative coated thereon, some of the microcapsules are ruptured by writing pressures or the like to cause the solvent, which contains the chromogenic reactant, to transfer to the surface which bears the color-developing agent, thereby allowing the chromogenic reactant and color-developing agent to undergo a reaction so that a color mark is obtained. On the other hand, heat-sensitive recording paper sheets, especially, heat-sensitive recording paper sheets generally called two-components color production systems are those obtained individually by separately dispersing a dyestuff precursor such as triphenylmethanephthalide-type or fluoran-type dyestuff precursor and an acidic phenol-type color-developing agent such as 2,2-bis(4'-hydroxyphenyl)propane (bisphenol A) or benzyl p-hydroxybenzoate into fine particles, adding a binder and other additives to the thus-prepared particulate dyestuff precursor and color-developing agent, and then applying the resultant coating formulation to a base material such as paper sheet or the like in such a way that the particulate dyestuff precursor is isolated from the particulate color-developing agent and vice versa. Color marks can be obtained through a reaction which takes place when either one or both of the particulate dyestuff precursor and color-developing agents are molten by heat to bring them into mutual contact.

There has also been disclosed a material which makes use of a dyestuff precursor as a temperatureindicating material along with an acidic substance and another substance which melts at a desired temperature. When the temperature reaches the desired temperature, the latter substance is molten and dissolves the dyestuff precursor and acidic substance so that they are brought into contact and hence allowed to undergo a reaction to produce a color, whereby indicating the temperature (Japanese Patent Laid-open No. 188528/1984).

Pressure- and heat-sensitive recording paper sheets, which are used widely and make use of color-producing reactions between phthalide- or fluoran-type dyestuff precursors and acidic color-developing agents as described above, however involve serious defective problems. Namely, (1) they require the dyestuff precursors and acidic color-developing agents in large amounts, resulting in a still-standing problem from the economical viewpoint. (2) The color fastness levels of produced color marks are insufficient so that these color marks are easily discolored, faded or even vanished upon exposure to light, heat or polar solvents.

With a view toward solving these problems, the present inventors have already proposed a novel color-producing system relying upon an oxidative color-producing mechanism which is totally different from conventional color-producing mechanisms (Japanese Patent Laid-open No. 107882/1982).

DISCLOSURE OF THE INVENTION

An object of this invention is to provide novel compounds, which are useful as oxidative color-developing agents in such a novel oxidative color-developing developing system, and their production process. A specific object of this invention is to provide oxidative color-developing agents, which upon contact with methine-type dyestuff precursors represented by the following general formula (III):

wherein X, Y and Z mean individually substituted or unsubstituted phenyl, substituted or unsubstituted naphthyl, substituted or unsubstituted β-styryl or substituted or unsubstituted aromatic and heterocyclic residual groups, X, Y and Z may be the same or different, and two of X, Y and Z may bonded together to form a ring, can cause the dyestuff precursors to produce their colors promptly and can hence provide stable color marks, as well as their production process.

It has been found that as oxidative color-developing agents capable of attaining such an object of this invention as mentioned above, novel benzoquinone derivatives represented by the following general formula (I):

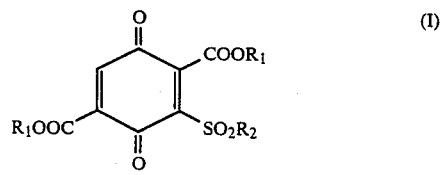

wherein $R_1$ means an alkyl or cycloalkyl group, $R_2$ denotes an alkyl or cycloalkyl group, a phenyl group which may optionally contain one or more halogen atoms and/or alkyl, cycloalkyl, alkoxy, alkylene, phenoxy, phenyl and/or biphenylyl groups, or a benzyl or naphthyl group which may optionally contain one or more methyl groups are extremely useful and can cause the above-described methine-type dyes of the general formula (III) to produce their colors extremely promptly and at high densities.

The novel benzoquinone derivatives of this invention and methine-type dyestuff precursors undergo such reactions as illustrated below. For example, their reactions proceed substantially irreversibly and stoichiometrically in much the same way as the following oxidation reaction, whereby providing color marks.

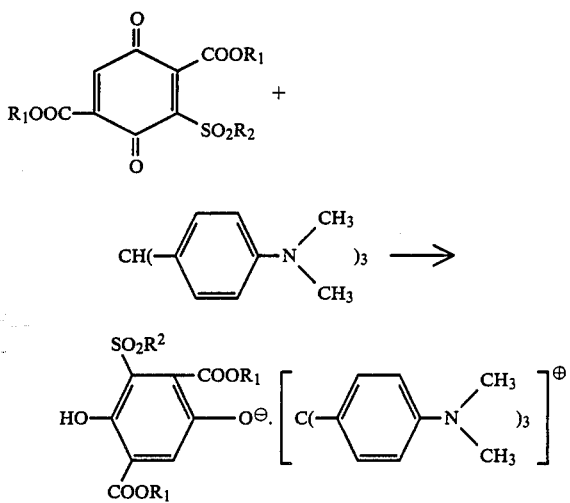

In pressure-sensitive recording paper sheets, heat-sensitive recording paper sheets or temperature-indicating indicating materials all of which make use of of the novel oxidative color-producing system, the novel benzoquinone derivatives of this invention may be used in small amounts as little as ⅓–1/50 of the amounts of conventional acidic color-developing agents required to cause coloring to lactone-type compound such as phthalide- or fluoran-type compound. In pressure-sensitive and heat-sensitive recording paper sheets, color marks obtained respectively by using the color-developing agents of this invention and methine-type dyestuff are extremely fast even when exposed to light, heat, polar solvents and the like.

DETAILED DESCRIPTION OF THE INVENTION

The novel benzoquinone derivatives of this invention are compounds represented by the general formula (I). As their specific examples, may be mentioned dimethyl 2-benzenesulfonyl-1,4-benzoquinone-3,6-dicarboxylate, diethyl 2-benzenesulfonyl-1,4-benzoquinone-3,6-dicarboxylate, di-n-butyl 2-benzenesulfonyl-1,4-benzoquinone-3,6-dicarboxylate, dicyclohexyl 2-benzenesulfonyl-1,4-benzoquinone-3,6-dicarboxylate, dimethyl 2-o-toluenesulfonyl-1,4-benzoquinone-3,6-dicarboxylate, diisobutyl 2-p-toluene-sulfonyl-1,4-benzoquinone-3,6-dicarboxylate, di-n-hexyl 2-p-toluenesulfonyl-1,4-benzoquinone-3,6-dicarboxylate, dioctyl 2-p-toluenesulfonyl-1,4-benzoquinone-3,6-dicarboxylate, di-n-octyl 2-p-toluenesulfonyl-1,4-benzoquinone-3,6-dicarboxylate, di-n-dodecyl 2-p-toluenesulfonyl-1,4-benzoquinone-3,6-dicarboxylate, dicyclohexyl 2-p-toluenesulfonyl-1,4-benzoquinone-3,6-dicarboxylate, diethyl 2-(3',4'-dimethylphenyl-sulfonyl)-1,4-benzoquinone-3,6-dicarboxylate, diethyl 2-(2', 5'-dimethylphenylsulfonyl)-1,4-benzoquinone-3,6-dicarboxylate, di-isobutyl 2-(2', 5'-dimethylphenyl-sulfonyl)-1,4-benzoquinone-3,6-dicarboxylate, diethyl 2-p-chlorophenylsulfonyl-1,4-benzoquinone-3,6-dicarboxylate, di-n-butyl 2-p-bromophenylsulfonyl-1,4-benzoquinone-3,6-dicarboxylate, di-isobutyl 2-(2',5'-dichlorophenylsulfonyl)-1,4-benzoquinone-3,6-dicarboxylate, dicyclohexyl 2-benzylsulfonyl-1,4-benzoquinone-3,6-dicarboxylate, diethyl 2-α-naphthylsulfonyl-1,4-benzoquinone-3,6-dicarboxylate, di-isobutyl 2-α-naphthylsulfonyl-1,4-benzoquinone-3,6-dicarboxylate, di-n-butyl 2-(4'-phenylsulfonyl)-1,4-benzoquinone-3,6-dicarboxylate, diethyl 2-α-tetralinsulfonyl-1,4-benzoquinone-3,6-dicarboxylate, diethyl 2-α-indanesulfonyl-1,4-benzoquinone-3,6-dicarboxylate, diethyl 2-(4-cyclohexylphenylsulfonyl)-1,4-benzoquinone-3,6-dicarboxylate, diethyl 2-p-methoxyphenylsulfonyl-1,4-benzoquinone-3,6-dicarboxylate, diethyl 2-p-phenoxyphenylsulfonyl-1,4-benzoquinone-3,6dicarboxylate, diethyl 2-n-butylsulfonyl-1,4-benzoquinone-3,6-dicarboxylate, di-isobutyl 2-cyclohexylsulfonyl-1,4-benzoquinone-3,6-dicarboxylate, di-isobutyl 2-benzylsulfonyl-1,4-benzoquinone-3,6-dicarboxylate, diethyl 2-β-phenethylsulfonyl-1,4-benzoquinone-3,6-dicarboxylate, etc. Also included are compounds corresponding to the chlorine derivatives and containing a fluorine or iodine atom instead of the chlorine atom.

The subject benzoquinone derivatives represented by the general formula (I) can be obtained by oxidizing hydroquinone derivatives represented by the following general formula (II):

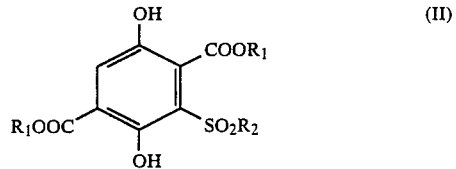

wherein $R_1$ and $R_2$ have the same meaning as defined above with respect to the general formula (I).

When quinone derivatives represented by the general formula (V) and sulfinic acid derivatives represented by the general formula (VI) are subjected to an addition reaction in a water-containing organic solvent, the hydroquinone derivatives represented by the general formula (II) are formed as shown by the following equation:

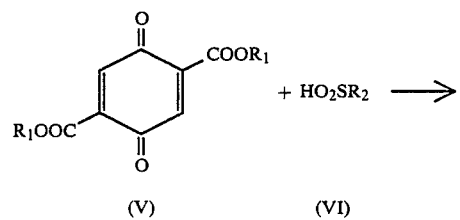

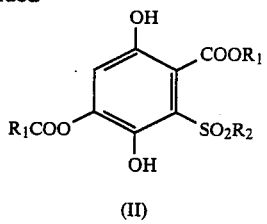

(II)

As examples of the benzoquinone derivative (V), may be mentioned dimethyl 1,4-benzoquinone-2,5dicarboxylate, diethyl 1,4-benzoquinone-2,5-dicarboxylate, dipropyl 1,4-benzoquinone-2,5-dicarboxylate, di-n-butyl 1,4-benzoquinone-2,5-dicarboxylate, di-isobutyl 1,4-benzoquinone-2,5-dicarboxylate, di-sec-butyl 1,4-benzoquinone-2,5-dicarboxylate, di-isoamyl 1,4-benzoquinone-2,5-dicarboxylate, di-n-amyl 1,4-benzoquinone-2,5-dicarboxylate, di-(2-methyl)butyl 1,4-benzoquinone-2,4-dicarboxylate, di-n-hexyl 1,4-benzoquinone-2,5-dicarboxylate, di-n-octyl 1,4-benzoquinone-2,5-dicarboxylate, di-2-ethylhexyl 1,4-benzoquinone-2,5-dicarboxylate, di-n-dodecyl 1,4-benzoquinone-2,5-dicarboxylate, di-cyclohexyl 1,4-benzoquinone-2,5-dicarboxylate, etc.

As examples of the sulfinic acid derivatives represented by the general formula (VI), may be mentioned methanesulfinic acid, ethanesulfinic acid, n-butane-1-sulfinic acid, t-butylsulfinic acid, cyclohexanesulfinic acid, benzenesulfinic acid, toluenesulfinic acid, xylenesulfinic acid, naphthalenesulfinic acid, diphenylsulfinic acid, terphenylsulfinic acid, anisole-sulfinic acid, diphenylethersulfinic acid, phenylcyclohexanesulfinic acid, tetralinsulfinic acid, indane sulfinic acid, benzylsulfinic acid and so on. The reaction between the benzoquinone derivative (V) and sulfinic acid derivative (VI) can proceed with a good yield if an aqueous solution or suspension of the sulfinic acid derivative (VI) and the benzoquinone derivative (V) in an amount substantially equivalent to the sulfinic acid derivative (VI) are heated and reacted in the presence of a water-containing organic solvent, namely, a mixture of water and an organic solvent, e.g., acetone, tetrahydrofuran, dioxane, benzene, toluene, xylene or the like.

Alternatively, the reaction may also proceed with a good yield when a solution of the benzoquinone derivative in an inert solvent (advantageously, an aromatic compound such as benzene, toluene or xylene) is reacted with an aqueous solution of the sulfinic acid derivative.

In the above reaction, it is preferred to use the sulfinic acid derivative (VI) in an amount of at least 1 mole, or preferably 1.2–2 moles per mole of the benzoquinone derivative (V). It is not necessary to use the sulfinic acid derivative in any large excess amount. The reaction temperature may be above 50° C. but below the boiling point of water. If the reaction is carried out at a low temperature, the yield of the hydroquinone derivative (II) will drop.

The progress of the reaction is very fast and the reaction can be brought to substantial completion in 1 hour. From the viewpoint of assuring a good yield, it will be sufficient to conduct the reaction for 4 hours or longer. Turning to the amount of the solvent to be used in the reaction, it may be enough to use the solvent in an amount at least equal to the amount of the benzoquinone derivative (V). It is not particularly advantageous even if the solvent is used in any large excess amount. It may be sufficient if the solvent is used in an amount of about 3–10 times by weight the amount of the benzoquinone derivative (V). Turning next to the amount of water to be required for dispersing the sulfinic acid derivative, it may be suitable to use water in an amount 3–10 times the sulfinic acid derivative (VI). Since the reaction product is allowed to precipitate as a solid matter when the organic solvent is removed from the liquid reaction mixture by steam distillation or direct distillation, it is then collected by filtration, dried, and purified by a method such as recrystallization. Since the compounds (II) are generally produced in forms readily soluble in methanol, it is most convenient to extract them with methanol and then to cause them to precipitate in water.

The thus-obtained hydroquinone derivatives of the general formula (II) are then oxidized to produce the novel benzoquinone derivatives of this invention.

As specific exemplary compounds represented by the general formula (II), may be mentioned dimethyl 2-benzenesulfonyl-3,6-dihydroxyterephthalate, diethyl 2-benzenesulfonyl-3,6-dihydroxyterephthalate, di-n-butyl 2-benzenesulfonyl-3,6-dihydroxyterephthalate, dicyclohexyl 2-benzenesulfonyl-3,6-dihydroxyterephthalate, dimethyl 2-o-toluenesulfonyl3,6-dihydroxyterephthalate, diisobutyl 2-p-toluene-sulfonyl-3,6-dihydroxyterephthalate, di-n-hexyl 2-p-toluenesulfonyl-3,6-dihydroxyphthalate, di-n-octyl 2-p-toluenesulfonyl-3,6-dihydroxyphthalate, di-n-dodecyl 2-p-toluenesulfonyl-3,6-dihydroxyphthalate, dicyclohexyl 2-p-toluenesulfonyl-3,6-dihydroxyterephthalate, diethyl 2-(3', 4'-dimethylphenylsulfonyl)-3,6-dihydroxyterephthalate, diethyl 2-(2', 5'-dimethylphenylsulfonyl)-3,6-dihydroxyterephthalate, diisobutyl 2-(2', 5'-dimethylphenylsulfonyl)-3,6-dihydroxyterephthalate, diethyl 2-p-chlorophenylsulfonyl-3,6-dihydroxyterephthalate, di-n-butyl 2-p-bromophenylsulfonyl-3,6-dihydroxyterephthalate, diethyl 2-(2',5'-dichlorophenylsulfonyl)-3,6-dihydroxyterephthalate, diethyl 2-α-naphthylsulfonyl-3,6-dihydroxyterephthalate, diisobutyl 2-β-naphthylsulfonyl-3,6-dihydroxyterephthalate, dicyclohexyl 2-benzylsulfonyl-3,6-dihydroxyterephthalate, di-n-butyl 2-(4'-phenylsulfonyl)-3,6-dihydroxyterephthalate, diethyl 2-β-tetralinsulfonyl-3,6-dihydroxyterephthalate, diethyl 2-β-indanesulfonyl-3,6-dihydroxyterephthalate, diethyl 2-(4'-cyclohexylphenylsulfonyl)-3,6-dihydroxytetrephthalate, diethyl 2-p-methoxyphenylsulfonyl-3,6-dihydroxyterephthalate, diethyl 2-p-phenoxyphenylsulfonyl-3,6-dihydroxyterephthalate, diethyl 2-n-butylsulfonyl-3,6-dihydroxyterephthalate, diisobutyl 2-cyclohexylsulfonyl-3,6-dihydroxyterephthalate, diisobutyl 2-benzylsulfonyl-3,6-dihydroxyterephthalate, diethyl 2-β-phenethylsulfonyl-3,6-dihydroxyterephthalate, and so on.

The benzoquinone derivatives represented by the general formula (I) can each be obtained by subjecting the corresponding starting compound (II) and an oxidizing agent to a heat treatment in an inert solvent at a temperature ranging from room temperature to the boiling point of the solvent.

As oxidizing agents useful in the practice of the above reaction, lead(IV) compounds such as lead peroxide, trilead tetroxide and lead tetraacetate, and manganese(IV) or manganese (III) compounds, for example, manganese dioxide, trimanganese tetroxide, manganese tetraacetate and dinitrogen tetroxide may be used suitably. These oxidizing agents may generally be used in an amount equimolar to excess based on the starting compound (II), or preferably in an amount of 2–10 moles per mole of the starting compound (II).

On the other hand, it is appropriate to use, as reaction solvents, nonpolar solvents, or preferably those having boiling points within the range of from 40° C. to 180° C. in amounts 2-10 times the amount of starting compound (II). As such reaction solvents, may be mentioned ligroin, n-hexane, n-heptane, isooctane, benzene, toluene, xylene, cumene, tetralin, carbon tetrachloride, chloroform, ethylene dichloride, trichloroethylene, monochlorobenzene, o-dichlorobenzene, etc. The reaction temperature may preferably be below 150° C., or preferably from room temperature to 110° C. The reaction time may be from 2 to several tens hours. It is not preferred to conduct the reaction at an elevated temperature and for a long period of time, because quinone undergoes decomposition under such conditions. After completion of the reaction, the oxidized reaction product contained in the liquid reaction mixture is separated from the oxidizing agent by filtration, the filtrate is concentrated, and a paraffinic solvent, for example, hexane or ligroin is added to the thus-concentrated filtrate. The filtrate is cooled so that the intended product is caused to deposit as crystals. After filtering and washing the intended product, the intended product is dried to obtain the intended product. The thus-obtained crystals are generally light yellowish and are generally stable in sunlight exposure. They are generally soluble in organic solvents and the resultant solutions are tinged light yellowish.

The compounds of this invention, for example, the material identified by Compound No. 30 in Table 2 was analyzed by elementary analysis and NMR spectrum. Its structure has been confirmed as follow:

(IV)

Molecular weight: 516.619

$C_{27}H_{32}SO_8$

Elementary analysis data (%):

|  | C | H | S |
|---|---|---|---|
| Calculated: | 62.77 | 6.24 | 6.21 |
| Found: | 63.29 | 6.15 | 5.91 |

Identification of hydrogen atoms by NMR spectrum:

It is apparent from the above structure that the peaks of its NMR spectrum correspond respectively to the 22 protons of the cyclohexyl groups, the 2 protons of the methylene moiety of the benzyl group, the 1 proton of the quinone nucleus, and the 5 protons of the benzene nuclei of the benzyl group.

Using a 100MH-NMR apparatus, its measurement was conducted at 80° C. in perchloroethylene. The following results were obtained.

0.86–2.12 ppm: Multiplet produced by the protons of the methylene moieties of the cyclohexyl groups. Corresponding to 20 protons (by integral).

4.57 ppm: Singlet produced by the $CH_2$ moiety of the benzyl group. Corresponding to 2 protons (by integral).

5.0 ppm: Multiplet produced by the $H\beta$s of the cyclohexyl groups. Corresponding to 2 protons (by integral).

6.93 ppm: Singlet produced by the $H\alpha$ of the quinone nucleus. Corresponding to 1 proton (by integral).

7.3 ppm: Singlet produced by the Hs of the benzene nucleus of the benzyl group. Narrow singlet. Corresponding to 5 protons (by integral).

No absorption corresponding to the proton of any OH group.

From the above results, it is apparent that the structure of the compound is shown by the above structural formula (IV).

When using the novel benzoquinone derivatives of this invention as color-developing agents, for example, color-developing agents for pressure-sensitive recording paper sheets, their solubility and dissolution velocities in hydrophobic solvents in which their corresponding dyestuff are dissolved affect their color-producing speeds upon recording. Therefore, some compounds are suitably selected from the benzoquinone derivatives of the general formula (I) for their use as color-developing agents by taking into consideration their miscibility to solvents in which the methine dyestuff of the general formula (III) are dissolved. On the other hand, as color-developing agents for heat-sensitive recording paper sheets, the melting points of dyestuff and color-developing agents employed in the heat-sensitive recording paper sheets govern the color-producing temperature characteristics of the heat-sensitive recording paper sheets. Accordingly, compounds having melting points within preferred color-producing temperature ranges are selected. Alternatively, the color-developing agents may be used in combination with a third component, namely, a sensitivity improver or a melting-point lowering agent to adjust the color-producing characteristics.

In order to produce pressure-sensitive recording paper sheets which contain a color-developing agent of this invention, conventionally-known application methods may all be used, including (A) to apply an water-base coating formulation, which makes use of an aqueous suspension of the color-developing agent, to a base such as a paper web by means of a coater, (B) to incorporate the color-developing agent in a base such as a paper web upon production of the paper web, and (C) to coat an ink (hereinafter called "color-developing ink", which has been prepared by either dissolving or suspending the color-developing agent in an organic solvent, all over a base or to locally print (spot-print) a base with the color-developing ink. It is usually preferred to coat the water-base coating formulation (A) or to coat the color-developing ink (C). The water-base coating formulation employed in the method (A) may be prepared by mixing an aqueous suspension of the color-developing agent, i.e., the benzoquinone derivative with various additives which may be incorporated as needed to adjust the properties as pressure-sensitive recording paper sheets, including (1) inorganic or organic pigments such as kaolins, calcium carbonate, aluminum hydroxide, colloidal silica, zinc oxide, titanium oxide, acid clays, polystyrene dispersion and/or urea resin fillers, (2) a dispersant such as a polyphosphoric salt or polyacrylic salt, (3) a water-soluble binder such as starch or denatured starch, or a binder such as synthetic or natural rubber latex emulsion or polyvinyl acetate, (4) various other additives such as fluorescent brightening agent, defoaming agent, viscosity modifier, dusting inhibitor, slime-controlling agent, lubricant and-/or waterproofing agent, so that the resulting coating formulation has viscosity and rheology characteristics conforming with a coating method to be followed.

For the preparation of the color-developing ink employed in the method (C), it is feasible to follow any preparation method which is routinely practised in the technical field of ink. Namely, an oil-base color-developing ink can be prepared by dissolving a pigment such as kaolin, aluminum hydroxide, zinc hydroxide or calcium carbonate in an organic solvent, for example, a lower alcohol, low molecular-weight ketone, a lower alkyl butyrate, methyl or ethyl cellosolve, benzene, toluene or the like and then adding the resultant pigment solution to the color-developing agent, followed by further addition of aids such as an oil-soluble cellulose derivative (nitrocellulose, acetylcellolose, ethylcellulose, or the like), polyvinyl chloride resin, polyvinyl acetate resin, polyvinyl butyral resin or the like as a binder, a dispersant, a blocking inhibitor and/or a plasticizer as needed.

The thus-prepared water-base coating formulation or color-developing ink is then coated on a base or printed on a base by a printing technique such as gravure, flexographic or offset printing technique, so that pressure-sensitive copying paper sheets containing the color-developing agent are obtained.

It is also possible to coat a layer of the color-developing agent on the same side of a base as microcapsules of a dyestuff so as to obtain single-sheet pressure-sensitive paper sheets each of which can by itself produce the color of the dyestuff (self-contained paper sheets).

When producing heat-sensitive recording paper sheets which contains one of the color-developing agents of this invention, it is possible to use, in combination with the dyestuff and the color-developing agent, an organic or inorganic pigment such as kaolin, calcined kaolin, talc, titanium oxide, calcium carbonate, zinc oxide, mica-family mineral, diatomaceous earth, urea-formaldehyde resin or the like, water-soluble binder, waterproofing agent, natural wax such as bees wax, shellac or the like, synthetic wax such as petroleum wax, paraffin wax, microcrystalline wax or polyethylene wax, metallic soap (as lubricant and smudge inhibitor) such as calcium stearate or zinc stearate, sensitivity improver such as stearic amide, palmitic amide or ethylenebisstearoamide, various surfactants, various defoaming agents, various background coloring inhibitors and/or the like in the coating formulation as needed, whereby to improve the coating applicability and heat-sensitive characteristics.

The color-developing agents of this invention feature great initial color-producing speeds. This means that they permit prompt appearance of marks upon printing. This feature is therefore very preferable for color-developing agents. Besides, they have a structural advantage from the safety viewpoint of routinely-employed compounds, because they do not contain any halogens. Furthermore, they exhibit good storability when coated on paper sheets. As mentioned above, the compounds of this invention have various advantages over conventional compounds of the same type.

When using one of these color-developing agents for a temperature-indicating material, the color-developing agent may generally be used in combination with microcapsules of a material having a desired melting point and a methine-type dyestuff precursor of the general formula (III). Thus, the resultant temperature-indicating material makes use of such a principle that subsequent to rupture of some of the microcapsules, the dyestuff precursor of the general formula (III) and color-developing agent undergo an irreversible color-producing reaction in the material molten at a temperature above the desired temperature. Such temperature-indicating materials can be effectively used for controlling the storage temperatures of chilled or frozen foods or the like by using a material, which has a melting point below room temperature, within microcapsules.

This invention will hereinafter be described in detail in the following Examples.

Some starting hydroquinones which are useful in the production of their corresponding benzophenone derivatives of this invention were synthetically prepared in the following manner.

In the following Examples, all designations of "part" or "parts" will mean part or parts by weight.

SYNTHESIS EXAMPLE 1

(Synthesis of dicyclohexyl 2-p-toluenesulfonyl-3,6-dihydroxyterephthalate)

Mixed were 1 part of dicyclohexyl 2,5-dioxyterephthalate, 3 parts of electrolytic manganese dioxide and 3 parts of benzene. The mixture was heated with stirring for 6 hours in a reactor equipped with a water trap while distilling and removing water. Then, the contents were hot-filtered, the manganese dioxide was washed with benzene, the filtrate and washing were combined together, the benzene was distilled off, ligroin was added to the residue, and the resultant solution was allowed to stand, thereby obtaining a crude quinone derivative with a crude yield of 80–90%. The crude quinone derivative had been quinonized to 30–60% or so, depending on the raw material. After determining its purity, the experiment moved to the next reaction step.

Five parts of sodium p-toluenesulfinate (hydrated crystals) were dissolved in 30 parts of water, followed by an addition of 2.5 parts of concentrated hydrochloric acid to free p-toluenesulfinic acid. Then, 6 parts (converted as 100% pure) of the above-obtained quinone derivative (about 80% of its stoichiometric amount) and 50 parts of acetone were added and the resultant mixture was stirred under reflux for 6 hours. Thereafter, the acetone was distilled off and the remaining mass was separated from the water layer. The mass was washed once with water. The thus-obtained solid matter was taken out and was then heated with stirring for 30 minutes with 50 parts of methanol. The resultant mixture was allowed to cool and while the contents were still warm, insoluble matter (dihydroxyterephthalic esters) was filtered off. The insoluble matter was washed with methanol and the filtrate and washing were combined together. The methanol was distilled off to obtain a viscous syrup. It was thereafter dissolved under heat in xylene, and the resultant xylene solution was allowed to cool down to room temperature, thereby allowing a white solid to deposit. The white solid was filtered off, washed with a small amount of xylene and then dried at 70° C. to obtain 8.5 parts (substantially stoichiometric compared with the yield of the quinone derivative) of white crystals having a melting point of 142°–144° C. Their elementary analysis data were as follows: Elementary analysis data (%):

Elementary analysis data (%):

| | C | H | S |
|---|---|---|---|
| Calculated: | 62.77 | 6.24 | 6.21 |
| Found: | 62.30 | 6.28 | 6.26 |

SYNTHESIS EXAMPLE 2

(Synthesis of di-n-octyl 2-p-toluenesulfonyl-3,6-dihydroxyterephthalate)

Di-n-octyl 2,5-dihydroxyterephthalate was quinonized in the same manner as in Synthesis Example 1. In this case, the ester was quinonized almost entirely. Then, following the procedure of Example 1, the quinone derivative was reacted with p-toluenesulfinic acid. A methanol extract of the reaction product was caused to evaporate to dryness, the residue was extracted with n-hexane, and the extract was caused to cool in an ice box, resulting in white crystals with an yield of about 80%. They were recrystallized from hexane, leading to a melting point of 76°–78° C. Their elementary analysis data were as follows: Elementary analysis data (%):

Elementary analysis data (%):

| | C | H | S |
|---|---|---|---|
| Calculated: | 64.56 | 7.69 | 5.56 |
| Found: | 64.47 | 7.97 | 5.36 |

SYNTHESIS EXAMPLE 3

(Synthesis of dicyclohexyl 2-cyclohexylsulfonyl-3,6-dihydroxyterephthalate)

The quinonization of dicyclohexyl 2,5-dihydroxyterephthalate was carried out in the same manner as in Synthesis Example 1. The reaction product was reacted with cyclohexylsulfinic acid in the same manner as in Synthesis Example 1. Following the procedure of Synthesis Example 1, the reaction product was extracted with methanol and water was added to the extract to such an amount that the extract was clouded at warm temperatures. The resultant solution was then stored in an ice box, resulting in deposition of crystals. The yield of these crude crystals was about 90%. They were thereafter recrystallized by dissolving them under heat in methanol, adding water at a warm temperature to the resultant methanol solution to make the latter develop turbidity, and then allowing the resultant mixture to cool. White crystals having a melting point of 175°–176° C. were obtained. Their elementary analysis data were as follows: Elementary analysis data (%):

Elementary analysis data (%):

| | C | H | S |
|---|---|---|---|
| Calculated: | 61.40 | 7.10 | 6.64 |
| Found: | 61.34 | 7.59 | 6.44 |

In the same manner, the various compounds given in Table 1 were also synthesized. The melting points of the thus-synthesized compounds are also given in Table 1.

TABLE 1

| Compound No. | Structure R | Structure X | Melting point (°C.) |
|---|---|---|---|
| 1 | $C_2H_5$ | phenyl | 220–221 |
| 2 | $C_2H_5$ | p-tolyl (-C6H4-CH3) | 212–214 |
| 3 | $C_2H_5$ | p-methoxyphenyl (-C6H4-OCH3) | 194–196 |
| 4 | i-$C_4H_9$ | p-tolyl (-C6H4-CH3) | 135–137 |
| 5 | i-$C_4H_9$ | naphthyl | 129–131 |
| 6 | i-$C_4H_9$ | -CH2-phenyl | 125–126 |
| 7 | i-$C_4H_9$ | 2,5-dimethylphenyl | 159–160 |
| 8 | n-$C_6H_{13}$ | p-tolyl (-C6H4-CH3) | -65 |
| 9 | n-$C_8H_{17}$ | p-tolyl (-C6H4-CH3) | 76–78 |
| 10 | cyclohexyl (H) | p-tolyl (-C6H4-CH3) | 147–149 |
| 11 | cyclohexyl (H) | biphenyl | 167–169 |
| 12 | cyclohexyl (H) | -C6H4-O-C6H5 | 204–206 |

TABLE 1-continued

| Compound No. | Structure R | Structure X | Melting point (°C.) |
|---|---|---|---|
| 13 | -⟨H⟩ | 2,4-dimethylphenyl (-C₆H₃(CH₃)₂) | 162–164 |
| 14 | -⟨H⟩ | naphthyl | 135–137 |
| 15 | -⟨H⟩ | $-CH_2-$phenyl | 163–165 |
| 16 | -⟨H⟩ | -⟨H⟩ | 175–176 |
| 17 | -⟨H⟩ | biphenyl | 150–152 |
| 18 | -⟨H⟩ | n-C₄H₉ | 90–92 |
| 19 | -⟨H⟩ | indanyl (benzene fused cyclopentane) | 130–132 |
| 20 | -⟨H⟩ | $-CH_2-$C₆H₄$-CH_3$ | 172–174 |

EXAMPLE 1

(Synthesis of diisobutyl 2-p-toluenesulfonyl-1,4-benzoquinone-3,6-dicarboxylate)

One part of diisobutyl 2-p-toluenesulfonyl-3,6dihydroxyterephthalate, 3 parts of electrolytic manganese dioxide and 5 parts of benzene were mixed. After allowing the mixture to stand for 24 hours, it was agitated at its boiling point for 3 hours. The reaction mixture was hot-filtered, and a portion of the benzene was distilled off to concentrate the filtrate to about ⅓ of its initial volume. Upon addition of ligroin, a yellowish precipitate was caused to deposit. The mixture was allowed to cool overnight at room temperature and the solid matter was collected by filtration. Then, it was washed with ligroin and dried at room temperature in air, thereby obtaining light-yellowish crystals having a melting point of 112°–114° C. with a yield of about 70%.

Their elementary analysis data were as follows:

| | Elementary analysis data (%): | | |
|---|---|---|---|
| | C | H | S |
| Calculated: | 59.73 | 5.67 | 6.93 |
| Found: | 59.55 | 5.59 | 6.84 |

EXAMPLE 2

(Synthesis of dicyclohexyl 2-benzylsulfonyl-1,4-benzoquinone-3,6-dicarboxylate [Compound No. 30])

One part of dicyclohexyl 2-benzylsulfonyl-3,6-dihydroxyterephthalate, 2 parts of electrolytic manganese dioxide and 3 parts of toluene were agitated at 35°–45° C. for 8 hours and then at its boiling point for additional 2 hours. The reaction mixture was hotfiltered and the volume of the resultant filtrate was concentrated to about ⅓. After adding ligroin to the concentrate, the resultant mixture was allowed to cool to obtain light-yellowish crystals with a yield of 60%. Upon recrystallization, they showed a melting point of 160°–162° C. Detailed analysis data of this compound, such as its elementary analysis data, are as described before.

EXAMPLE 3

Various benzoquinone derivatives were obtained in the same manner. The thus-synthesized compounds and their melting points are shown in Table 2.

TABLE 2

| Compound No. | Structure R | Structure X | Melting point (°C.) |
|---|---|---|---|
| 21 | C₂H₅ | $-SO_2-$phenyl | 112–114 |
| 22 | i-C₄H₉ | $-SO_2-$phenyl | 100–102 |
| 23 | i-C₄H₉ | $-SO_2-$C₆H₄$-CH_3$ | 112–114 |
| 24 | n-C₈H₁₇ | $-SO_2-$C₆H₄$-CH_3$ | 75–77 |
| 25 | -⟨H⟩ | $-SO_2-$C₆H₄$-CH_3$ | 135–137 |
| 26 | -⟨H⟩ | $-SO_2-$naphthyl | 129–130 |
| 27 | -⟨H⟩ | $-SO_2-$biphenyl | 115–117 |
| 28 | -⟨H⟩ | $-SO_2-$C₆H₄$-O-$C₆H₅ | 129–131 |
| 29 | -⟨H⟩ | $-SO_2-$(2,4-dimethylphenyl) | 133–134 |

TABLE 2-continued

| Compound No. | Structure R | Structure X | Melting point (°C.) |
|---|---|---|---|
| 30 | —⟨H⟩ | —SO₂—CH₂—⟨ ⟩ | 160–162 |
| 31 | —⟨H⟩ | —SO₂—⟨H⟩ | 124–126 |
| 32 | —⟨H⟩ | —SO₂—C₄H₉ | 88–90 |
| 33 | C₂H₅ | —SO₂—CH₂—⟨ ⟩ | 142–144 |
| 34 | —⟨H⟩ | —SO₂—⟨ ⟩—CH₂\CH₂/CH₂ | 146–147 |
| 35 | —⟨H⟩ | —SO₂—⟨ ⟩—⟨ ⟩ (with phenyl) | 179–181 |
| 36 | —⟨H⟩ | —SO₂—⟨ ⟩—OCH₃ | 106–108 |
| 37 | —⟨H⟩ | —SO₂—⟨ ⟩—⟨H⟩ | 138–140 |
| 38 | —⟨H⟩ | —SO₂CH₂—⟨ ⟩—CH₃ | 148–150 |

EXAMPLE 4

Results similar to those of Example 1 were obtained by following the procedure of Example 1 except that 10 parts of lead peroxide were used in place of the manganese dioxide. Similar results were also obtained when carbon tetrachloride was used in lieu of the benzene, 2 parts of dinitrogen tetroxide were added with ice-cooling, and the resultant mixture was stirred for 1 hour.

EXAMPLE 5

Using as a color-developing agent di-isobutyl 2-p-toluenesulfonyl-1,4-benzoquinone-3,6-dicarboxylate (m.p. 112°–114° C.) which had in advance been wet-ground in the presence of an anionic high-molecular surfactant, a water-base coating formulation having the following weight composition and a solid content of 40% was prepared

| | Parts by dry weight |
|---|---|
| Kaolin-clay | 85 |
| Calcium carbonate | 15 |
| Color-developing agent (used as an aqueous dispersion) | 4 |
| Styrene-butadiene latex (used as an aqueous dispersion) | 6 |
| Oxidized starch (used as an aqueous solution) | 6 |

The water-base coating formulation was coated to a high-quality paper web by a Meyer bar to give a dry coat weight of 6 g/m², thereby producing CF-sheet for pressure-sensitive recording paper sheets.

On the side, phenylxylylethane (trade name: Nisseki Highsol SAS-296; product of Nippon Petrochemical Co., Ltd.) containing 3 wt. % of tris(4dimethylaminophenyl)methane (Leuco Crystal Violet) was microencapsulated by a complex coacervation process which made use of gelatin-carboxymethylcellulose films, so that a microcapsule suspension having a solid content of 18% (by weight) and containing microcapsules of 7 μm in average particle size was obtained. One hundred parts by weight of this microcapsule suspension were mixed thoroughly with 5 parts by weight of wheat starch particles having an average particle size of 15 μm, 5 parts by weight of a 20% (by weight concentration) aqueous solution of cooked and oxidized starch and 1 part by weight of tris-N-(2-hydroxyethyl)-amine into a water-base white coating formulation. It was then coated to high-quality paper web by a Meyer bar to give a dry coat weight of 5 g/m². Upon drying, CB-sheets for pressure-sensitive recording were produced. By combining these CF-sheets and CB-sheets, their performances were evaluated.

EXAMPLES 6–8

CF-sheets for pressure-sensitive recording were produced in the same manner as in Example 1 except that di-cyclohexyl 2-p-toluenesulfonyl-1,4-benzoquinone-3,6dicarboxylate (m.p. 135°–137° C.), diethyl 2-benzene-sulfonyl-1,4-benzoquinone-3,6-dicarboxylate (m.p. 112°–114° C.) and di-n-octyl 2-p-toluenesulfonyl-1,4-benzo-quinone-3,6-dicarboxylate (m.p. 75°–77° C.) were used respectively. Their performances were evaluated in combination with CB-sheets for pressure-sensitive recording, which had been produced in the same manner as in Example 5.

COMPARATIVE EXAMPLE 1

CF-sheets for pressure-sensitive recording were produced in the same manner as in Example 5 except that diisobutyl 2,5-di-p-toluenesulfonyl-1,4-benzoquinone-3,6-dicarboxylate was used as a color-developing agent. Their performances were evaluated in combination with CB-sheets for pressure sensitive recording, which had been produced in the same manner as in Example 5.

COMPARATIVE EXAMPLE 2

A water-base coating formulation having the following composition and a solid content of 40% was prepared by using a p-phenylphenol-formaldehyde condensation product (trade name: RBE-40; product of Mitsui Toatsu Chemicals, Incorporated) as a color-developing agent.

| | Parts by dry weight |
|---|---|
| Kaolin | 85 |
| Calcium carbonate | 15 |
| Color-developing agent (used as an aqueous dispersion) | 20 |
| Styrene-butadiene latex (used as an aqueous dispersion) | 6 |
| Oxidized starch (used as an aqueous solution) | 6 |

From the above coating formulation, CF-sheets were produced in the same manner as in Example 5. These CF-sheets were combined with commercial CB-sheets for pressure-sensitive copying (trade name: Mitsubishi- NCR N-40; product of Mitsubishi Paper Mills, Ltd.) and their performances were evaluated.

Testing Method for Pressure-Sensitive Recording Paper Sheets (1) Color-producing performance:

The coated sides of each CF-sheet and CB-sheet in each of the Examples and Comparative Examples were placed in contiguous juxtaposition to each other and were typed by an electric typewriter to produce their color.

Measurement of the density of each produced color was effected by measuring its reflectivity with a TSS-type Hunter colorimeter (manufactured by Toyo Seiki Seisakusho, Ltd.). Measurements were conducted respectively upon an elapsed time of 30 seconds (initial color density) and upon an elapsed time of 48 hours (final color density), both after the color was produced by typing their respective CF-sheet and CB-sheet with the typewriter. Representing the reflectivities before the color production, 30 seconds after the color production and 48 hours after the color production by $I_0$, $I_1$ and $I_2$ respectively, the color production percents were calculated by the following equations:

Initial color production percent
$(J_1) = (I_0 - I_1)/I_0 \times 100$ (%)

Final color production percent $(J_2) = (I_0 - I_2)/I_0 \times 100$ (%)

It is indicated that the color-producing speed is faster and the color-density is higher as the initial color production percent and final color production percent become greater and their difference becomes smaller.

(2) Light-resistant color fastness:

The above paper sheets which had been caused to produce colors by the typewriter were exposed for 2 hours to a carbon-arc fadometer (manufactured by Suga Testing Machine Co., Ltd.). The reflectivity of each paper sheet was measured by the Hunter colorimeter both before and after the test. Its light-resistant color fastness was expressed in terms of the color production percent after the exposure. The disappearance of marks after their exposure to light becomes less as the percent remainder of produced color after the exposure becomes higher.

(3) Resistance of produced color marks to plasticizer:

The color-produced surface of each CF-sheet was brought into close contact with a polyvinyl chloride sheet of a commercial pocket file, which polyvinyl chloride sheet contained dioctyl phthalate as a plasticizer. After holding the CF-sheet and polyvinyl chloride sheet for 24 hours in a constant-temperature compartment of 60° C. while applying a load of 1 kg per 100 cm$^2$, the polyvinyl chloride sheet was removed and the color density of the CF-sheet was compared with its color density before the test to investigate the change in color density. The produced color density was measured right after the test and 1 month (stored in a dark place) after the test, respectively. Less reduction in color density after the test means greater resistance of produced color marks to polar solvents such as plasticizers. It is thus preferred to show smaller reduction in color density after the test. (4) Yellowing tendency of CF-sheets:

The yellowing susceptibility of surfaces coated with acidic color-developing agents, which had been widely employed, in pressure-sensitive recording paper sheets making use of the color-developing agents in an oxidizing gas atmosphere such as NO$_x$ were determined in the following manner. Namely, CF-sheets were exposed for 60 minutes in an NO$_x$ gas atmosphere in accordance with JIS-L-1055-1941 (Testing Method of Fastness of Dyed Materials and Dyes to Nitrogen Oxide Gases). The yellowing tendency of each CF-sheet was expressed in terms of the degree of its yellowing after the test.

Test results

Test results of the pressure-sensitive recording paper sheets prepared respectively in Examples 5–8 and Comparative Examples 1–2 are as follows:

|  | Density of produced color | | Fastness of produced color marks | | Yellowing of CF-sheet |
|---|---|---|---|---|---|
|  | Initial | Final | Light resistance | Plasticizer resistance |  |
| Ex. 5 | 43.1 | 45.1 | 37.1 | 45.5 | None |
| Ex. 6 | 42.9 | 44.9 | 36.8 | 45.1 | None |
| Ex. 7 | 42.8 | 44.4 | 36.7 | 45.0 | None |
| Ex. 8 | 43.2 | 44.9 | 35.9 | 44.8 | None |
| Comp. Ex. 1 | 32.0 | 43.8 | 29.0 | 43.5 | None |
| Comp. Ex. 2 | 30.6 | 35.3 | 28.5 | 17.0 | Severe |

From the above results, it is clear that the pressure-sensitive recording paper sheets making use of the compounds of this invention have superior performance to those employing conventional color-developing agents, namely, gave higher initial color densities than that making use of the similar quinone derivative (Comparative Example 1), exhibited greater resistance to light and the plasticizer compared with the pressure-sensitive recording paper sheet making use of the acid-base color production system (Comparative Example 2), and showed no yellowing tendency on the surfaces of their CF-sheets.

EXAMPLE 9

A color-developing dispersion was prepared by processing 10 g of dicyclohexyl 2-p-toluenesulfonyl-1,4-benzoquinone-3,6-dicarboxylate, 40 g of a 10% aqueous solution of polyvinyl alcohol (trade name: Kuraray Poval #217; product of Kuraray Co., Ltd.) and 50 g of water in a sand grinding mill.

On the side, 10 g of α,α, α', α'-tetrakis-(1'-ethyl-2'-methylindol-3'-yl)-1,4-xylene was pulverized in the same manner as the color-developing agent to obtain a dyestuff dispersion.

By using the dyestuff dispersion, a water-base coating formulation of the following composition (solid content: 15%):

|  | Parts by dry weight |
|---|---|
| Color-developing agent | 8 |
| Dyestuff | 7 |
| Stearic amide | 20 |
| Calcium carbonate | 65 |
| Polyvinyl alcohol | 20 |

The above-coating formulation was applied to a high-quality paper web to give a coat weight of 8 g/m$^2$, and the thus-coated paper web was then dried to produce heat-sensitive recording paper sheets.

COMPARATIVE EXAMPLE 3

A comparative sample was produced in exactly the same manner as in Example 9 except that 2,5-dibenzoyl-1,4-benzoquinone was used as a color-developing agent.

The heat-sensitive recording paper sheets of Example 9 were tinged only slightly, while those obtained in Comparative Example 3 were considerably colored yellowish. The latter heat-sensitive recording paper sheets were thus very inferior in appearance to the former ones.

Test results

The heat-sensitive recording paper sheets of Example 9 and Comparative Example 3 were each printed all over its surface by a thermal printer with an impression voltage of 20 V and current-feeding time period of 1.4 msec. (repetition cycle: 1.78 msec.). The color production percents of the thus-colored paper sheets were measured. The following color production percents were obtained. (Measurement was effected by using a green filter as they produced red colors.)
Example 9: 59.0%
Comparative Example 3: 39.4%

From the above results, it is understood that the compound of Example 9 has better color-developing effects than that of Comparative Example 3.

The compounds of this invention can serve as color-developing agents for oxidative color-producing systems making use of the principle of color production disclosed in Japanese Patent Application No. 183878/1980. Compared with color marks produced by conventional acid-base color-producing systems, the color-producing systems making use of the color-developing agents of this invention can provide color marks having very superior stability to light, water and organic solvents. The color-developing agents of this invention are still effective even when used in small amounts as little as ⅓–1/50 of the amounts of color-developing agents in such conventional systems. Compared with the color-developing agents already proposed by the inventors of this application and having structures similar to the color-developing agents of this invention, the color-developing agents of this invention have such merits that they have faster initial color-producing speeds, are free of halogen atoms, and provide color marks having higher densities.

EXAMPLE 10

A water-base coating formulation (used as a 30% aqueous dispersion) having the below-given composition was applied by a Meyer bar coater to a synthetic paper web containing polypropylene as a base material(trade name: UPO FPG-90; product of Oji-Yuka Co., Ltd.) to give a dry coat weight of 6 g/m2, whereby forming a color-developing layer.

| | Parts by dry weight |
|---|---|
| Kaolin | 60 |
| Synthetic calcium carbonate | 40 |
| Dispersant | 0.4 |
| Binder | |
| Polyvinyl alcohol | 6 |
| (used as an aqueous solution) | |
| SBR latex | 8 |
| (used s an aqueous dispersion) | |
| Oxidinzing material* | 4 |
| (used as a water-base dispersion) | |

*Oxidizing material: di-isobutyl 2-benzylsulfonyl-1,4-benzoquinone-3,6-dicarboxylate An acrylic emulsion containing acrylonitrile and butyl acrylate as its principal components was diluted to 20%, and then coated over the color-developing layer to give a dry coat weight of 2.5 g/m² so as to provide a spacer layer. An aqueous suspension, which had been obtained by finely wet-comminuting 4,4'-bis(N-methyl-N-benzylamino)-4''-N-dimethylamino-triphenylmethane in the presence of small amounts of triethanol amine and polyvinyl alcohol, was coated additionally over the spacer layer to give a dry coat weight of 1 g/m². The thus-coated suspension layer was dried to provide a layer which contained the methine-type dyestuff precursor. Thereafter, an adhesive surface which had been prepared by coating an acrylic emulsion-type adhesive formulation to a silicone-treated parting glassine paper web of 80 g/m² and then drying the thus-coated adhesive formulation was applied to the back surface of the above-coated synthetic paper web, thereby obtaining a printing paper web.

Then, a water-base ink of 40 wt. % solid content was prepared in accordance with the following composition.

| | Parts by solid weight |
|---|---|
| Microcapsules of hydrophobic organic solvent (used as an aqueous dispersion)** | 100 |
| SBR latex (used as an aqueous dispersion) | 20 |
| Hydroxyethylcellulose (used as an. aqueous solution) | 2 |
| Polyacrylamide (used as an aqueous solution) | 0.5 |

**Microcapsules of ethyl myristate in melamine resin walls

The above ink was spot-printed to different parts of the top layer of the above-mentioned printing paper web, which layer contained the methine-type dyestuff precursor, by using a printing screen frame made of a 150-mesh polyester fiber screen. The printed parts had a dry coat weight of 10 g/m². The screen-printed web was punched into labels to obtain temperature-indicating labels.

When exposed to temperatures above 7° C. after the microcapsules of the labels were ruptured to make them ready for use, the parts printed with microcapsules of ethyl myristate were gradually turned into a bluish purple color. The labels of this Example are extremely useful as labels for easily finding out storage temperature history below room temperature.

We claim:
1. Benzoquinone derivative represented by the following general formula (I):

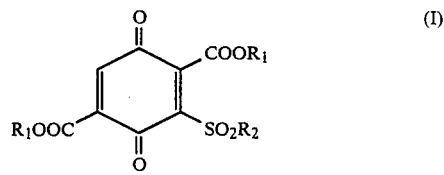

wherein $R_1$ is a $C_2$ to $C_8$ alkyl or cyclohexyl group, and $R_2$ is a $C_2$ to $C_4$ alkyl or cyclohexyl group, a benzyl group which can optionally contain one or more methyl groups, a napthyl group which can optionally contain one or more methyl groups, or a phenyl group which can optionally contain methyl, methoxy, cyclohexyl, $C_3$ cyclic alkylene, phenoxy, phenyl and/or biphenyl groups.

2. A process for producing a benzoquinone derivative represented by the followng general formula (I):

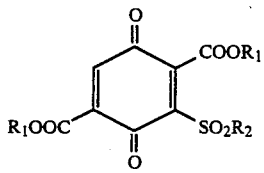
(I)

wherein $R_1$, is a $C_1$ to $C_8$ alkyl or cyclohexyl group, and $R_2$ is a $C_2$ to $C_4$ alkyl or cyclohexyl group, a benzyl group which can optionally contain one or more methyl groups, a napthyl group which can optionally contain one or more methyl groups, or a phenyl group which can optionally contain methyl, methoxy, cyclohexyl, $C_3$ cyclic alkylene, phenoxy, phenyl and/or biphenyl groups, which comprises oxidizing, in an inert solvent a hydroquinone derivative represented by the following general formula (II):

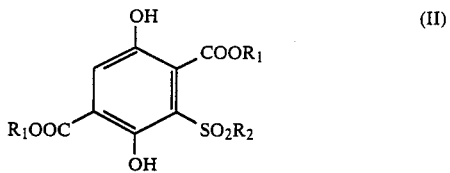
(II)

wherein $R_1$ and $R_2$ have the same meaning as defined above, with a lead (IV) compound, a manganese (III) compound or a manganese (IV) compound in an amount of 2 to 10 moles per mole of the hydroquinone derivative at a temperature below 150° C.

3. A process as claimed in claim 2 wherein the inert solvent is a non-polar solvent boiling within the range of from 40° to 180° C.

4. A process as claimed in claim 2 wherein the inert solvent is used in an amount 2 to 10 times the amount of the hydroquinone derivative.

5. A process as claimed in claim 2 wherein the reaction temperature ranges from room temperature to 110° C.

* * * * *